(12) United States Patent
Majmudar

(10) Patent No.: US 8,268,345 B2
(45) Date of Patent: Sep. 18, 2012

(54) MULTIPURPOSE HYDROGEL COMPOSITIONS AND PRODUCTS

(75) Inventor: Advait Majmudar, Vadodara (IN)

(73) Assignee: Transdermal Innovations Inc., North Brunswick, NJ (US)

( * ) Notice: Subject to any disclaimer, the term of this patent is extended or adjusted under 35 U.S.C. 154(b) by 651 days.

(21) Appl. No.: 12/315,498

(22) Filed: Dec. 3, 2008

(65) Prior Publication Data

US 2010/0055153 A1    Mar. 4, 2010

Related U.S. Application Data

(60) Provisional application No. 61/093,837, filed on Sep. 3, 2008.

(51) Int. Cl.
  *A61F 13/00*  (2006.01)
  *A61K 9/70*   (2006.01)
  *A61K 51/00*  (2006.01)
  *A61L 9/04*   (2006.01)
  *A61M 36/14*  (2006.01)

(52) U.S. Cl. ....... 424/443; 424/76.3; 424/1.25; 524/916

(58) Field of Classification Search .......... 424/443, 424/76.3, 1.25; 524/916
See application file for complete search history.

(56) References Cited

U.S. PATENT DOCUMENTS

| | | | |
|---|---|---|---|
| 4,460,562 A | 7/1984 | Keith et al. | |
| 4,593,053 A | 6/1986 | Jevne et al. | |
| 4,871,490 A | 10/1989 | Rosiak et al. | |
| 5,456,745 A | 10/1995 | Roreger et al. | |
| 5,514,379 A * | 5/1996 | Weissleder et al. | 424/426 |
| 5,622,168 A | 4/1997 | Keusch et al. | |
| 7,008,635 B1 | 3/2006 | Coury et al. | |
| 2003/0170308 A1* | 9/2003 | Cleary et al. | 424/486 |
| 2005/0095296 A1 | 5/2005 | Lowman et al. | |

FOREIGN PATENT DOCUMENTS

| IN | 192136 A1 | 2/2004 |
|---|---|---|
| WO | WO 01/30407 A1 * | 5/2001 |

OTHER PUBLICATIONS

International Search Report, PCT/US2008/013369, dated Apr. 29, 2009.
Murat Sen, Esra Nazan Avcy Published online Jun. 16, 2005 in Wiley InterScience, www.interscience.wiley.com. DOI: 10.1002/jbm.a. 30308.
Relleve L, Yoshii F, De la Rosa A, Kume T. Die Ang Makromol Chem 1999;273:63-68.
Jinghua Y, Xue C, Alfonso GC, Turturro A, Pedemonte E.. Polymer 1997;38(9): 2127-2133.
Zhai M, Yoshii F, Kume T, Hashim K.. Carbohydr Polym 2002;50(3): 295-303.
Jing R, Yanqun Z, Jiuqiang L, Hongfei H. Radiat Phys Chem 2001;62:277-281.
Khoo CG, Frantzich S, Rosinski A, Maria Sjöström M, Hoogstraate J. Oral gingival Eur J Pharm Biopharm 2003; 55:47-56.
Ju HK, Kim SY, Lee YM. Polymer 2001;42: 6851-6857.
Higa OZ, Rogero SO, Machado LDB, Mathor MB, Lugao AB. Radiat Phys Chem 1999;55:705-707.
Razzak et el Radiation Physics & Chemistry 62, 2001, 107-113 & ibid 55,1999, pp. 153-165.
Babolsar, I.R. Iran.0 Lakouraj M.M. et al. Iranian Polymer Journal / vol. 14 No. 12 (2005).
Wu et al., Journal of Radioanalytical and Nuclear Chemistry, 250(2); 391-395 (2001).
Thomas et al., J. Biomed Mater Res., 67A; 1329-1337 (2001).
Abd El-Mohdy et al., Journal of Polymer Research Reports, 11 pages, Apr. 18, 2008.
Nho et al., Journal of Applied Polymer Science, 90(6); 1477-1485 (2003).
M.M. Lakouraj et al., "Synthesis and Swelling Characterization of Cross-linked PVP/PAV Hydrogels", Iranian Polymer Journal 14 (12) 2005, pp. 1022-1030.

* cited by examiner

*Primary Examiner* — Isis Ghali
(74) *Attorney, Agent, or Firm* — Lerner, David, Littenberg, Krumholz & Mentlik, LLP

(57) ABSTRACT

Disclosed are sterile hydrogel compositions comprising polyvinyl alcohol ("PVA"), polyvinyl pyrrolidone ("PVP"), and a polysaccharide, wherein the combined amount of PVA and PVP present in the hydrogel compositions is from about 2% to about 12% weight by volume, based on the total volume of the composition, and wherein the hydrogel compositions has a gel fraction greater than or equal to 97%. Sterile hydrogel products including such sterile hydrogel compositions, and methods of making such sterile hydrogel compositions and sterile hydrogel products.

22 Claims, No Drawings

MULTIPURPOSE HYDROGEL COMPOSITIONS AND PRODUCTS

CROSS-REFERENCE TO RELATED APPLICATIONS

This application claims the benefit of the filing date of U.S. Provisional Patent Application No. 61/093,837 filed Sep. 3, 2008, the disclosure of which is hereby incorporated herein by reference.

BACKGROUND OF THE INVENTION

Hydrogels are used in the biomedical field in wound care, dental care, burn care, and for controlled drug delivery systems. Hydrogels are also used in ophthalmic applications, such as contact lenses. Hydrogels prepared from hydrophilic polymers are effective in wound care because they are biocompatible and provide a sterile moist cover, and because they have a relatively high water content and properties that closely resembles living tissues. (See, Murat Sen and Esra Nazan Avcý, published online 16 Jun. 2005, in Wiley InterScience (www.interscience.wiley.com), DOI: 10.1002/jbm.a.30308.) Moreover, the ideal hydrogels would be soft, mechanically strong, yet pliable to be able to take up body contours.

The same properties also make hydrogels useful in cosmetic applications and they may be used as structuring agents, moisturizers, and/or anti-scar agents. Even though hydrogels used in cosmetic applications need not be sterile, the absence of polymerization byproducts would be a great advantage. In particular, hydrogels have the capacity to prevent scar formation and to control moisture. These properties make hydrogels desirable for rejuvenating skin, and in particular, facial skin.

Hydrogels are typically prepared by crosslinking of hydrophilic polymers. Generally, crosslinking of the polymer chains is produced by hydroxyl free radicals, generated by chemical crosslinkers and initiators, or by ionizing radiation.

In chemical crosslinking, the hydroxyl free radicals are generated by the addition of chemical crosslinkers and initiators to a solution of the polymers. Hydrogels prepared by chemical crosslinking generally have very low mechanical strength and hence must have a supporting material, e.g., a film, foam or gauze, to make them useful for most applications. Moreover, chemical crosslinking leaves unreacted initiators and crosslinkers and byproducts of the chemical reaction, which are either toxic, undesirable, or both. These contaminants require additional purification steps which are expensive and time consuming. Moreover, as a general rule, such hydrogels cannot be sterilized easily.

In radiation induced crosslinking, an aqueous solution of the hydrophilic polymers is irradiated with, for example, gamma rays. Advantageously, the ionizing radiation simultaneously crosslinks and sterilizes the hydrogel. Typically, conventional hydrogels must be packaged and shipped with the plastic molds or trays in which they were crosslinked and/or sterilized, which adds more cost to the production and shipment of the hydrogel, and which produces environmentally unfriendly waste.

SUMMARY OF THE INVENTION

A first aspect of the present invention is directed to a hydrogel composition comprising polyvinyl alcohol ("PVA"), polyvinyl pyrrolidone ("PVP"), and one or more polysaccharides, wherein the combined amount of PVA and PVP present in the hydrogel composition is from about 2% to about 12% weight by volume ("(w/v)"), based on the total volume of the composition, and wherein the hydrogel composition has a gel fraction greater than or equal to about 97%.

A second aspect of the present invention is directed to a method of making a hydrogel composition comprising:
a) forming a solution by dissolving:
   i) Polyvinyl alcohol ("PVA"),
   ii) Polyvinyl pyrrolidone ("PVP"),
   iii) One or more polysaccharides, and
   iv) optionally, a preservative and/or another hydrophilic polymer
in water; and
b) setting the solution to form a thermoreversible gel matrix;
c) crosslinking the thermoreversible gel matrix to produce a hydrogel composition,
wherein the combined amount of PVA and PVP present in the hydrogel composition is from about 2% to about 12% weight by volume, based on the total volume of the composition, and wherein the hydrogel composition has a gel fraction greater than or equal to about 97%.

The hydrogel compositions of the present invention have a very wide range of applicability. That is, unlike PVA-polysaccharide hydrogels, they can contain additives such as humectants, preservatives, drugs, etc. in significant amounts, and form ideal hydrogels over wide range of operational/production parameters. Unlike PVP-polysaccharide hydrogels, the hydrogel compositions of the present invention have high mechanical strength (PVP-polysaccharide gels have very low strength (Sen and Avcý)). Hence, the hydrogel compositions of the present invention exhibit a combination of the superior mechanical strength of PVA-polysaccharide gels and the adaptability of PVP-polysaccharide gels.

The hydrogel compositions of the present invention also have a very high gel fraction, i.e., high degree of crosslinking. The high degree of crosslinking further contributes to the high mechanical strength of the hydrogel compositions of the present invention. Moreover, the high degree of crosslinking also results in hydrogel compositions having less surface irregularities as compared to prior hydrogels. Thus, the hydrogel compositions of the present invention are less likely to shed a portion of the hydrogel when used, for example, in a wound healing product.

Due to abovementioned properties, the hydrogel compositions of the present invention are capable of being affixed to a backing material, e.g., coated onto fabric or foam (to make, for example, a lightweight first aid kit for fire victims), while still retaining their sterility. The method of making a hydrogel composition of the present invention also allows for the production of sterile hydrogels without the need for any backing material. In certain embodiments, the sterile hydrogel compositions of the present invention may be prepared without any purification or sterilization step.

DETAILED DESCRIPTION

Polyvinyl alcohol ("PVA") is a water-soluble polymer, having the following structure:

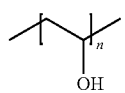

PVA is nontoxic, extremely biocompatible and commonly used in foods, pharmaceuticals, textile, adhesives, and water absorbent products. PVA is commercially available in various molecular weights and degrees of hydrolysis. The PVA used in one aspect of the present invention generally has a molecular weight of about 15 kDa to about 125 kDa, and may be fully or partially hydrolyzed. Preferably, the PVA has a molecular weight of about 125 kDa and a degree of hydrolysis of about 88%.

Polyvinyl pyrrolidone ("PVP") is a water-soluble polymer, having the following structure:

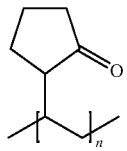

PVP is nontoxic and commonly used in pharmaceuticals, personal care products, and adhesives. PVP is commercially available in various molecular weights and degrees of hydrolysis. The PVP used in one aspect of the present invention generally has a molecular weight of about 40 kDa to about 1,300 kDa. Preferably, the PVP has a molecular weight of about 360 kDa.

Amounts of PVA in the hydrogel composition generally range from about 1% to about 5% (w/v), preferably from about 2% to about 4% (w/v), and more preferably about 3% (w/v), based on the total volume of the composition. Amounts of PVP in the hydrogel composition generally range from about 1% to about 8% (w/v), preferably from about 3% to about 5% (w/v), and more preferably about 4%, based on the total volume of the composition. The combined amounts of PVA and PVP in the hydrogel composition generally range from about 2% to about 12% (w/v) and preferably from about 5% to about 9% (w/v), based on the total volume of the composition.

Polysaccharides useful in the present invention include natural and synthetic polysaccharides and include disaccharides and oligosaccharides. Examples include carrageenan, agar-agar, chitosan, starch, maltose, lactose, sucrose, trehalose, palatinose, reducing malt sugar, reducing palatinose, reducing lactose, starch syrup, isomaltooligosaccharides, fructooligosaccharides, milk sugar oligosaccharides, soybean oligosaccharides, xylooligosaccharides, coupling sugar, cyclodextrin compounds, pullulan, pectin, konnyaku mannan, and polydextrose, xanthan gum, and mixtures thereof. Preferred polysaccharides are k-carrageenan, agar-agar, chitosan, starch, and/or mixtures thereof. The polysaccharide is present in the compositions of the present invention in amounts generally ranging from about 1% to about 4% (w/v), and preferably from about 1% to about 3% (w/v), based on the total volume of the composition.

"Gel faction" as used herein means the percentage of the total PVA and PVP in the hydrogel that is crosslinked into a gel structure. Typically, to determine the gel fraction, the hydrogel is dried until a constant weight is achieved to remove the water. The mass of the dried hydrogel is measured. The dried hydrogel, is then extracted with a solvent, such as water, to remove any PVA and PVP that is not crosslinked, which is water soluble. The extracted hydrogel is again dried to a constant weight. The mass of the extracted, dried hydrogel is then measured. Gel fraction may be calculated as follows:

Gel Fraction=$M_1/M_0 \times 100$, where $M_0$ is the mass of the dried hydrogel and $M_1$ is the mass of the extracted, dried hydrogel. The hydrogel compositions of the present invention have a gel fraction of greater than or equal to about 97%, preferably greater than or equal to about 98%, and more preferably greater than or equal to about 99%.

In an embodiment of the present invention, the hydrogel composition contains about 3% (w/v) of PVA, about 4% (w/v) of PVP, and about 1.5% (w/v) of carrageenan, agar-agar, or a combination thereof, based on the total volume of the composition.

In an embodiment of the present invention, the hydrogel composition contains
 a) from about 2% to about 4% weight by volume of PVA, based on the total weight of the composition;
 b) from about 3% to about 5% weight by volume of PVP, based on the total weight of the composition;
 c) from about 1% to about 4% weight by volume, based on the total weight of the composition, of κ-carrageenan, agar-agar, or a combination thereof; and
 d) optionally, from about 0.02% to about 0.6% weight by volume, based on the total weight of the composition, of methylparaben, propylparaben, or a mixture thereof.

The hydrogel compositions of the present invention generally contain about 90% water and are capable of absorbing about 160% to about 200% of their wet weight.

The compositions of the present invention may also include an additional hydrophilic polymer, which replaces PVP in part. As with the combined amounts of PVA and PVP described above, the total amounts of hydrophilic polymer in the hydrogel composition generally range from about 2% to about 12% (w/v), and preferably from about 5% to about 9% (w/v), based on the total volume of the composition. If an additional hydrophilic polymer is added, then water sorption increases to about 350% of the wet weight of hydrogel.

Examples of additional hydrophilic polymers useful in the hydrogel compositions of the present invention include polyacrylic acid, acryl amide, polyacryl amide, polyethylene oxide, carbopol, and mixtures thereof. Amounts of additional hydrophilic polymer in the hydrogel compositions of the present invention generally range from about 0.1% to about 3% (w/v), and preferably from about 0.5% to about 1% (w/v), based on the total volume of the composition.

Compositions of the present invention may also contain any cosmetic, dermatologic, or pharmaceutic additive, and in general may contain any physiologically acceptable additive. Examples of classes of additives include preservatives; drugs and active agents; antibiotics; antifungals; humectants; antioxidants; water-sorption enhancing agents; compositions that produce gas on irradiation; free-radical producing agents; and mixtures thereof.

Examples of preservatives useful in the present invention include parabens, sorbates, and benzoates. Amounts of preservatives in the hydrogel compositions of the present invention may range from about 0.01% to about 0.5% (w/v), and preferably from about 0.02% to about 0.3% (w/v), based on the total volume of the composition.

Examples of drugs and active agents useful in the present invention include growth factors, proteins, enzymes, synthetic anesthetics, analgesics, antiadrenergics, antiarrhythmics, anticholinergic agents, cholinomimetic agents, anticonvulsant agents, antidepressants, antiepileptics, antiviral agents, antiinflammatory agents, antimuscarinic agents, muscarinic agents, antineoplastic agents, antipsychotic agents, anxiolytics, hormones, hypnotics, immunosuppressive agents, immunoactive agents, neuroleptic agents, neuron blocking agents, antihypertensive agents, nutrients, vitamins, minerals sedatives, and steroids and derivatives thereof. Amounts of drugs and active agents in the hydrogel compositions of the present invention may range from about 0.01% to about 20%, preferably from about 0.1%% to about 10%, more preferably from about 0.5% to about 5%, even more preferably from about 1% to about 3% (w/v), based on the total volume of the composition.

Examples of antibiotics useful in the present invention include idoxuridine, trifluorouddine, vidarabine pyrimethamine, bismuth tribromophenate, bacitracin, erythromycin, and tetracycline. Amounts of antibiotics in the hydrogel compositions of the present invention may range from about 0.01% to about 20%, preferably from about 0.1%% to about 10%, more preferably from about 0.5% to about 5%, even more preferably from about 1% to about 3% (w/v), based on the total volume of the composition.

Examples of antifungals useful in the present invention include caspofungin, clotrimazole, fluconazole, flucytosine, butenafine, ciclopirox, econazole, ketoconazole, miconazole, naftifine, nystatin, oxiconazole, terbinafine, ionic, colloidal or silver salts, iodine, and tolnaftate. Amounts of antifungals in the hydrogel compositions of the present invention may range from about 0.01% to about 20%, preferably from about 0.1%% to about 10%, more preferably from about 0.5% to about 5%, even more preferably from about 1% to about 3% (w/v), based on the total volume of the composition.

Examples of humectants useful in the present invention include polythene glycols (PEG), propylene glycol and glycerols. Amounts of humectants in the hydrogel compositions of the present invention may range from about 0.01% to about 20%, preferably from about 0.1%% to about 10%, more preferably from about 0.5% to about 5%, even more preferably from about 1% to about 3% (w/v), based on the total volume of the composition.

Examples of antioxidants useful in the present invention include vitamin A, vitamin C, vitamin E, flavonoids, and carotenoids. Amounts of antioxidants in the hydrogel compositions of the present invention may range from about 0.01% to about 20%, preferably from about 0.1%% to about 10%, more preferably from about 0.5% to about 5%, even more preferably from about 1% to about 3% (w/v), based on the total volume of the composition.

Examples of water-sorption enhancing agents useful in the present invention include Polyacrylates, Acrylates, Acryl amide, Polyacryl amide, and Carbomers. Amounts of water-sorption enhancing agents in the hydrogel compositions of the present invention may range from about 0.01% to about 20%, preferably from about 0.1%% to about 10%, more preferably from about 0.5% to about 5%, even more preferably from about 1% to about 3% (w/v), based on the total volume of the composition.

An example of a composition that produces gas on irradiation useful in the present invention includes ammonium carbonate. Amounts of compositions that produce gas on irradiation in the hydrogel compositions of the present invention may range from about 0.01% to about 20%, preferably from about 0.1%% to about 10%, more preferably from about 0.5% to about 5%, even more preferably from about 1% to about 3% (w/v), based on the total volume of the composition.

Examples of free-radical producing agents useful in the present invention include persulfates and peroxides. Amounts of free-radical producing agents in the hydrogel compositions of the present invention may range from about 0.01% to about 20%, preferably from about 0.1% to about 10%, more preferably from about 0.5% to about 5%, even more preferably from about 1% to about 3% (w/v), based on the total volume of the composition.

The hydrogel compositions of the present invention exhibit excellent mechanical and shear strength. For example, the hydrogel compositions of the present invention generally have a mechanical strength of greater than about 400 $g/cm^2$, and preferably greater than about 700 $g/cm^2$. The mechanical strength of hydrogels may be determined by machines available in the market for testing material strength, such as those manufactured by Instron (Norwood, Mass.).

In some embodiments, the hydrogel compositions of the present invention may be affixed to a backing material to form a hydrogel product. Because the hydrogel compositions of the present invention have superior versatility, they are capable of being coated onto a backing material such as a fabric or foam while still retaining their sterility. Thus, the hydrogel compositions of the present invention may be advantageously used in wound care products, drug delivery systems, and cosmetic products.

Examples of hydrogel products of the present invention include wound dressings; bandages; fire blankets; absorbent sponges; systems for delivering an active agent such as, for example, a drug delivery patch; and cosmetics, e.g., cosmetic wipes for cleansing or moisturizing and face masks for rejuvenation of facial skin. Backing materials useful in the hydrogel products of the present invention include, for example, cloths, fabrics, meshes, foils, foams, nets, and combinations thereof. Representative backing materials include plastics, natural or synthetic fibers, paper, and metals.

Generally, the hydrogel compositions of the present invention are prepared by forming an aqueous solution of PVA, PVP, and a polysaccharide. The solution is then set to form a thermoreversible gel matrix. Setting the solution may be accomplished by any known means, such as by cooling the solution.

The thermoreversible gel matrix is then crosslinked to form a hydrogel composition. Crosslinking may be accomplished by any means known in the art, including, for example, radiation induced crosslinking, ultraviolet induced crosslinking, chemical crosslinking, freezing and thawing crosslinking. Preferably, crosslinking is accomplished by ionizing radiation, such as by ultraviolet radiation, electron beam radiation, or gamma radiation.

In an embodiment of the invention, any desired additional hydrophilic polymers and/or additives may be added to the aqueous solution, e.g., at the same time as the PVA, PVP, and polysaccharide are added, or at some time during the crosslinking of the thermoreversible gel matrix.

In certain embodiments, the solution is formed by dissolving the PVA in hot water and allowing the solution to cool to room temperature. The PVP and polysaccharide (and any desired additional hydrophilic polymers and additives) are then added to the solution, and are completely dissolved with slow stirring. In certain embodiments, the solution is then allowed to sit for several hours, e.g., overnight, to allow the hydrophilic polymers to swell.

In certain embodiments, the polysaccharide acts as a thermoreversible setting agent, allowing the solution to set into thermoreversible gel matrix. However, the polysaccharides become active thermosreversible setting agents only when the solution is heated. For example, if carrageenan, agar, or a mixture thereof is used, the solution must be heated to at least 80° C. for the carrageenan, agar, or a mixture thereof to become an active thermoreversible setting agent. Thus, in certain embodiments, the solution is heated, preferably to a temperature from about 80° C. to about 120° C., and more preferably to about 90° C.

If the elevated temperature is maintained for a prolonged period, the polysaccharide may deteriorate in quality and may impart a yellowish tinge to the hydrogel. Thus, in certain embodiments, the solution is maintained at the elevated temperature for a short period of time. Preferably, the elevated temperature is maintained for a period of from about 1 minute to about 10 minutes. Furthermore, the solution is preferably slowly stirred during heating.

The heated solution is then cooled, preferably to about 60° C. to about 70° C., more preferably to about 60° C., and poured into molds of the desired shape and size. In certain embodiments, a suitable backing material may be placed inside the molds prior to introduction of the solution.

The solution is then cooled in the mold to about room temperature or below, preferably from about 15° C. to about 25° C. Upon cooling to room temperature or below, the solution sets to form a firm thermoreversible gel matrix. This thermoreversible gel matrix may be easily removed from the mold, along with any backing material, while maintaining its shape. In an embodiment of the present invention, the amount of solution poured into the mold is sufficient to produce a hydrogel composition having a thickness of from about 0.5 mm to about 6 mm as required by the application.

In certain embodiments, the thermoreversible gel matrix, either with or without the mold, is then sealed in an airtight container. The airtight container may be made in any form and of any material suitable to maintain the hydrogel in a sterile condition until the sealed airtight container is breached. For example, the container may be in the form of a pouch, a box, an envelope, a cylinder, or a bag and may be made of plastic, paper, or metal. The thermoreversible gel sealed in the container is then irradiated by ionizing radiation, which simultaneously crosslinks and sterilizes the thermoreversible gel to form a sterile hydrogel composition.

The ionizing radiation useful in the present invention includes gamma radiation, e.g., from $Co^{60}$. Alternatively, the source of the ionizing radiation may be an electron beam or ultraviolet radiation. In certain embodiments, the ionizing radiation is applied in a dose of from about is 15 kGy to about 65 kGy, and preferably about 25 kGy. In another embodiment, the process can be automated such that the solution is applied to the backing material in a continuous process by machine, cut to desired shapes and sizes, and sealed in airtight containers, which are then irradiated at desired doses.

In certain embodiments of the invention, the crosslinking may be performed in two steps. First, the thermoreversible gel matrix is irradiated with ionizing radiation at a dose of about 5 kGy to about 15 kGy to form a partially crosslinked thermoreversible gel matrix. The partially crosslinked thermoreversible gel matrix is then irradiated a second time with ionizing radiation, this time at a dose of from about is 10 kGy to about 60 kGy, in order to completely crosslink and sterilize the thermoreversible gel matrix to form a sterile hydrogel composition. In an embodiment of the present invention, a sterile hydrogel composition containing an additive is produced by introducing the additive into the partially crosslinked thermoreversible gel matrix after the first dose of ionizing radiation and prior to the second dose of ionizing radiation.

The simultaneous crosslinking and sterilization of the hydrogel composition by ionizing radiation while sealed inside an airtight container simplifies production and eliminates the use of the chemical crosslinkers and initiators required in chemical crosslinking. In embodiments of the present invention, a preservative may be incorporated into the solution or into the thermoreversible gel matrix in small quantities. The preservative advantageously provides the hydrogel composition or hydrogel product with enhanced resistance to contamination in case the sealed airtight container is accidentally breached prior to use, or in case the hydrogel composition or product is left exposed due to oversight or unavoidable circumstances.

In certain embodiments, the methods of the present invention, by the formation of the thermoreversible gel matrix, allow the solution to be removed from its mold prior to being sealed in the airtight container and irradiated. This eliminates the need for disposable trays, thus reducing production costs, environmentally unfriendly waste, shipping weight and cost, and the need for the user to remove the hydrogel composition or hydrogel product from the tray and dispose of the tray, thus making it very user friendly.

Moreover, conventional processes for making hydrogels require that the open side of the molds or trays be covered with an upper flap prior to being sealed in the airtight container and irradiated. The use of the upper flap requires a separate production step and increases the cost of production. In these conventional processes, the composition of the upper flap material, as well as the composition of the mold, is critical in determining the overall quality of the hydrogel produced after irradiation. In some instances, the upper flap may stick strongly to the surface of the hydrogel, or the gel may stick too strongly to the mold surface, which results in the rejection of the hydrogel or makes the hydrogel difficult or impossible to use by the consumer. For example, in a conventional PVA-Polysaccharide gel, mold made from Polypropylene (PP) or high density polyethylene (HDPE) and an upper flap of polyester of particular mesh size will work. However, the same material will not work for conventional PVP-Polysaccharide gels, which require a Polyethylene terephthalate (PET) mold and a PP upper flap.

In certain embodiments, the method of making a sterile hydrogel composition of the present invention eliminates the need for an upper flap. Omitting the upper flap eliminates a production step, thereby reducing the cost and the time for production. Omitting the upper flap also eliminates the possibility of manufacturing defects in which the upper flap sticks to the surface of the hydrogel, which can result in consumer dissatisfaction and waste.

An embodiment of the present invention is a method of making a sterile hydrogel composition includes the steps of
  a) forming a solution by mixing:
    i) from about 2% to about 4% weight by volume, based on the total volume of the composition, of polyvinyl alcohol having a molecular weight of 125 kDa and a degree of hydrolysis of about 88%,
    ii) from about 3% to about 5% weight by volume, based on the total volume of the composition, of polyvinyl pyrrolidone having a molecular weight of 360 kDa,
    iii) from about 1% to about 4% weight by volume, based on the total volume of the composition, of K-carrageenan or agar-agar or a combination thereof, and
    iv) optionally, from about 0.02% to about 0.3% weight by volume, based on the total volume of the composition, of methylparaben, propylparaben, or a mixture thereof,
  into water;
  b) heating the solution to about 90° C. for about 1 to about 10 minutes;
  c) pouring the solution into a mold;
  d) cooling the solution in the mold to about 15° C. to about 25° C. to form a thermoreversible gel matrix;

e) optionally, removing the thermoreversible gel matrix from the mold;
f) sealing the thermoreversible gel matrix in an airtight container; and
g) irradiating the thermoreversible gel matrix in the sealed container with ionizing radiation at a dose of about 25 kGy, to produce a sterile hydrogel composition that remains sterile until the sealed, airtight container is breached, wherein the sterile hydrogel composition has a gel fraction greater than or equal to about 97%.

In certain embodiments, the thermoreversible gel matrix may be sealed in the airtight container under a vacuum or in an inert gas atmosphere, such as nitrogen, argon, or nitrous oxide.

The following examples are intended to further illustrate the present invention. They are not intended to limit the invention in any way. Unless otherwise indicated, all parts are by weight.

EXAMPLE 1

3% w/v PVA (molecular weight 125 kDa; degree of hydrolysis 88%) is dissolved with stirring in de-ionized, hot water. The solution is cooled to room temperature. 4% w/v PVP (molecular weight 360 kDa; K90), 1.75% w/v κ-carrageenan, 0.05% w/v methyl paraben, and 0.03% w/v propyl paraben are added to the solution and the solution is stirred until all components are dissolved. The solution is allowed to stand over night at room temperature. The solution is heated to about 90° C. and the temperature is maintained for 5 to 10 minutes.

The hot solution is cooled to about 60° C. and poured into a mold. If a backing material is desired, a backing material, such as a woven or non-woven fabric, a net, or a mesh made of synthetic or natural (e.g., cotton) material, is placed within the mold prior to introduction of the hot solution. The solution and mold are further cooled to about 15° C. to set the thermoreversible gel.

The thermoreversible gel is then removed from the mold and sealed in suitable pouches. The sealed thermoreversible gel is then crosslinked and sterilized by irradiation with ionizing radiation at a dose of 25-30 kGy to form a sterile hydrogel composition.

The hydrogels are good quality and have excellent mechanical strength and pliability.

EXAMPLE 2

3% w/v PVA (molecular weight 125 kDa; degree of hydrolysis 88%) is dissolved with stirring in de-ionized, hot water. The solution is cooled to room temperature. 4% w/v PVP (K-90; molecular weight 360 kDa), 2.5% w/v κ-carrageenan, 0.05% w/v methyl paraben, 0.03% w/v propyl paraben, and 1% w/v carbomer, acryl amide, or polyacrylic acid are added to the solution and the solution is stirred until all components are dissolved. The solution is allowed to stand over night at room temperature. The solution is heated to about 90° C. and the temperature is maintained for 5 to 10 minutes.

The hot solution is cooled to about 60° C. and poured into a mold. If a backing material is desired, a backing material, such as a woven or non-woven fabric, a net, or a mesh made of synthetic or natural (e.g., cotton) material, is placed within the mold prior to introduction of the hot solution. The solution and mold are further cooled to about 15° C. to set the thermoreversible gel.

The thermoreversible gel is then removed from the mold and sealed in suitable pouches. The sealed thermoreversible gel is then crosslinked and sterilized by irradiation with ionizing radiation at a dose of 25-30 kGy to form a sterile hydrogel composition.

The addition of the carbomer, acryl amide, or polyacrylic acid results in a hydrogel composition with much higher water absorbing properties over a comparable hydrogel without the carbomer, acryl amide, or polyacrylic acid. A high quality hydrogel is produced.

EXAMPLE 3

3% w/v PVA (molecular weight 125 kDa; degree of hydrolysis 88%) is dissolved with stirring in de-ionized, hot water. The solution is cooled to room temperature. 4% w/v PVP (K-90; molecular weight 360 kDa), 1.5% w/v κ-carrageenan, 0.05% w/v methyl paraben, 0.03% w/v propyl paraben, and 1% w/v carbomer, acryl amide or polyacrylic acid are added to the solution and the solution is stirred until all components are dissolved. The solution is allowed to stand over night at room temperature. The solution is heated to about 90° C. and the temperature is maintained for 5 to 10 minutes.

The hot solution is cooled to about 60° C. and poured into a mold. If a backing material is desired, a backing material, such as a woven or non-woven fabric, a net, or a mesh made of synthetic or natural (e.g., cotton) material, is placed within the mold prior to introduction of the hot solution. The solution and mold are further cooled to about 15° C. to set the thermoreversible gel.

The thermoreversible gel is then removed from the mold and sealed in Low Density Polyethelene (LDP) bags. The sealed thermoreversible gel is then crosslinked and sterilized by irradiation with ionizing radiation at a dose of 40-45 kGy to form a sterile hydrogel composition.

The addition of the carbomer, acryl amide, or polyacrylic acid results in a hydrogel composition with much higher water absorbing properties over a comparable hydrogel without the carbomer, acryl amide, or polyacrylic acid.

EXAMPLE 4

3% w/v PVA (molecular weight 125 kDa; degree of hydrolysis 88%) is dissolved with stirring in de-ionized, hot water. The solution is cooled to room temperature. 4% w/v PVP (K-90; molecular weight 360 kDa), 2.5% w/v κ-carrageenan, 0.05% w/v methyl paraben, 0.03% w/v propyl paraben, and 500 PPM of ammonium carbonate are added to the solution and the solution is stirred until all components are dissolved. The solution is allowed to stand over night at room temperature. The solution is heated to about 90° C. and the temperature is maintained for 5 to 10 minutes.

The hot solution is cooled to about 60° C. and poured into a mold. If a backing material is desired, a backing material, such as a woven or non-woven fabric, a net, or a mesh made of synthetic or natural (e.g., cotton) material, is placed within the mold prior to introduction of the hot solution. The solution and mold are further cooled to about 15° C. to set the thermoreversible gel.

The thermoreversible gel is then removed from the mold and sealed in suitable pouches. The sealed thermoreversible gel is then crosslinked and sterilized by irradiation with ionizing radiation at a dose of 25-30 kGy to form a sterile hydrogel composition.

The addition of the ammonium carbonate results in the production of carbon dioxide during crosslinking, which results in a hydrogel composition with a microporous structure. This method produces a microporous hydrogel that has very high water sorption due to very high surface area produced by the micropores. A high-quality microporous hydrogel is produced.

All publications cited in the specification are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A sterile hydrogel composition comprising polyvinyl alcohol ("PVA"), polyvinyl pyrrolidone ("PVP"), and a polysaccharide, wherein the PVA is present in an amount of from 2% to 4% weight by volume based on the total volume of the composition; the PVP is present in an amount of from 3% to 5% weight by volume based on the total volume of the composition; the polysaccharide is selected from the group consisting of κ-carrageenan, agar-agar, and a combination thereof and present in an amount of 1% to 4% weight by volume based on the total volume of the composition; and the sterile hydrogel composition has a gel fraction greater than or equal to 97%, wherein the sterile hydrogel composition is produced by forming an aqueous solution of the PVA, The PVP and the polysaccharide; setting the solution to form a thermoreversible gel matrix; and simultaneously crosslinking and sterilizing the thermoreversible gel matrix by irradiation with ionizing radiation at a dose of from about 15 kGy to about 65 kGy.

2. The sterile hydrogel composition of claim 1, wherein the sterile hydrogel composition has a gel fraction greater than or equal to 99%.

3. The sterile hydrogel composition of claim 1, further comprising an additional hydrophilic polymer.

4. The sterile hydrogel composition of claim 3, wherein the additional hydrophilic polymer is selected from the group consisting of polyacrylic acid, acryl amide, polyacryl amide, polyethylene oxide, carbopol, and mixtures thereof.

5. The sterile hydrogel composition of claim 1, further comprising an additive selected from the group consisting of preservatives, drugs and active agents, antibiotics, antifungals, humectants, gelling agents, antioxidants, water-sorption enhancing agents, compositions that produce a gas upon irradiation, free-radical producing agents, and mixtures thereof.

6. The sterile hydrogel composition of claim 5, wherein the preservative is selected from the group consisting of parabens, sorbates, benzoates, and mixtures thereof.

7. The sterile hydrogel composition of claim 5, wherein the humectant is selected from the group consisting of polyethylene glycol, propylene glycol, glycerols, and mixtures thereof.

8. The sterile hydrogel composition of claim 1 having a mechanical strength greater than about 400 grams/square centimeter.

9. The sterile hydrogel composition of claim 1 having a mechanical strength greater than about 700 grams/square centimeter.

10. A hydrogel product comprising the sterile hydrogel composition of claim 1 affixed to a backing material.

11. The hydrogel product of claim 10, wherein the backing material is selected from the group consisting of cloth, fabric, tape, foam, plastic, paper, and combinations thereof.

12. The hydrogel product of claim 10, wherein the hydrogel product is selected from, the group consisting of cosmetic products, burn treatment products, fire blankets, absorbent sponges, drug or active agent delivery products, bandages, and wound dressings.

13. The sterile hydrogel composition of claim 1, wherein the PVA is present in an amount of 3% weight by volume, the PVP is present in an amount of 4% weight by volume, and the polysaccharide is present in an amount of 1.5% weight by volume, based on the total volume of the composition.

14. A method of making a sterile hydrogel composition comprising:
   a) forming an aqueous solution by dissolving:
      i) polyvinyl alcohol ("EVA"),
      ii) polyvinyl pyrrolidone ("PVP"),
      iii) a polysaccharide, and
      iv) optionally, a preservative in water;
   b) setting the solution to form a thermoreversible gel matrix;
   c) simultaneously crosslinking and sterilizing the thermoreversible gel matrix by irradiation with ionizing radiation at a dose of from about 15 kGy to about 65 kGy,
   wherein the PVA is present in an amount of from 2% to 4% weight by volume based on the total volume of the composition; the PVP is present in an amount of from 3% to 5% weight by volume based on the total volume of the composition; the polysaccharide is selected from the group consisting of κ-carrageenan, agar-agar, and a combination thereof and present in an amount of 1% to 4% weight by volume based on the total volume of the composition; and the sterile hydrogel composition has a gel fraction greater than or equal to 97%.

15. The method of claim 14, wherein the setting step b) comprises:
   b1) heating the solution to an elevated temperature; and
   b2) cooling the solution to a temperature at or below room temperature to form the thermoreversible gel matrix.

16. The method of claim 14, further comprising applying a backing material to the solution or the thermoreversible gel matrix before irradiation or to the hydrogel after irradiation to form a sterile hydrogel product.

17. The method of claim 14, further comprising sealing the thermoreversible gel matrix within an airtight container prior to irradiation.

18. The method of claim 14, further comprising introducing an additive into the solution or the thermoreversible gel matrix before or during the simultaneously crosslinking and sterilizing.

19. The method of claim 14, wherein the simultaneously crosslinking and sterilizing step c) comprises:
   c1) irradiating the thermoreversible gel matrix with ionizing radiation at a dose of from about 5 kGy to about 15 kGy to form a partially crosslinked thermoreversible gel matrix; and
   c2) irradiating the partially crosslinked thermoreversible gel matrix with ionizing radiation at a dose of from about 10 kGy to about 60 kGy to sterilize and completely crosslink the thermoreversible gel matrix; and
further comprising introducing an additive into the partially crosslinked thermoreversible gel matrix produced by irradiating step c1) before irradiating step c2) to form a sterile hydrogel composition containing the additive.

20. A method of making a sterile hydrogel composition comprising:
  a) forming an aqueous solution by mixing:
    i) from 2% to 4% weight by volume of polyvinyl alcohol ("PVA"), based on the total volume of the composition,
    ii) from 3% to 5% weight by volume of polyvinyl pyrrolidone ("PVP") based on the total volume of the composition,
    iii) from 1% to 4% weight by volume of polysaccharide selected from the group consisting of κ-carrageenan, agar-agar, and a combination thereof based on the total volume of the composition, and
    iv) optionally, from 0.04% to 0.6% weight by volume of methylparaben, propylparaben, or a mixture thereof based on the total volume of the composition, and
    v) water;
  b) heating the solution to about 90° C. for about 1 to about 10 minutes;
  c) pouring the solution into a mold;
  d) cooling the solution in the mold to about 15° C. to about 25° C. to form a thermoreversible gel matrix;
  e) optionally, removing the thermoreversible gel matrix from the mold;
  f) sealing the thermoreversible gel matrix in an airtight container; and
  g) irradiating the thermoreversible gel matrix in the sealed container with ionizing radiation at a dose from about 15 kGy to about 65 kGy,
to produce the sterile hydrogel composition that remains sterile until the sealed, airtight container is breached, wherein the sterile hydrogel composition has a gel fraction greater than or equal to 97%.

21. The method according to claim 14, wherein the amount of PVA is 3% weight by volume, the amount of PVP is 4% weight by volume, and the amount of the polysaccharide is 1.5% weight by volume.

22. The method according to claim 20, wherein the sterile hydrogel composition has a gel fraction greater than or equal to 99%.

* * * * *

UNITED STATES PATENT AND TRADEMARK OFFICE
CERTIFICATE OF CORRECTION

PATENT NO. : 8,268,345 B2
APPLICATION NO. : 12/315498
DATED : September 18, 2012
INVENTOR(S) : Advait Majmudar It is certified that error appears in the above-identified patent and that said Letters Patent is hereby corrected as shown below:

In the Claims

Col. 12, Claim 12, Line 7, delete the ","

Col. 12, Claim 14, Line 20, "EVA" should read --PVA--

Signed and Sealed this
Eighteenth Day of March, 2014

Michelle K. Lee
*Deputy Director of the United States Patent and Trademark Office*